(12) United States Patent
Terazaki et al.

(10) Patent No.: US 8,062,629 B2
(45) Date of Patent: Nov. 22, 2011

(54) HAIR COSMETIC COMPOSITION

(75) Inventors: Hiroyuki Terazaki, Sumida-ku (JP); Masako Ueno, Sumida-ku (JP)

(73) Assignee: Kao Corporation, Tokyo (JP)

( * ) Notice: Subject to any disclaimer, the term of this patent is extended or adjusted under 35 U.S.C. 154(b) by 1278 days.

(21) Appl. No.: 10/367,889

(22) Filed: Feb. 19, 2003

(65) Prior Publication Data

US 2003/0147824 A1    Aug. 7, 2003

Related U.S. Application Data

(63) Continuation of application No. 09/908,575, filed on Jul. 20, 2001, now abandoned.

(30) Foreign Application Priority Data

Jul. 21, 2000 (JP) ................................. 2000-220668
Jul. 28, 2000 (JP) ................................. 2000-229539

(51) Int. Cl.
*A61Q 5/00* (2006.01)
*A61Q 5/12* (2006.01)

(52) U.S. Cl. ................ 424/70.1; 424/70.27; 424/70.28; 514/63; 514/557; 514/715; 514/724

(58) Field of Classification Search .............. 424/70.1, 424/401, 70.27, 70.28; 514/63, 557, 715, 514/724
See application file for complete search history.

(56) References Cited

U.S. PATENT DOCUMENTS

| | | | |
|---|---|---|---|
| 4,369,037 A * | 1/1983 | Matsunaga et al. .......... 8/127.51 |
| 4,777,037 A | 10/1988 | Wagman et al. |
| 4,839,162 A * | 6/1989 | Komori et al. .................. 424/63 |
| 4,954,335 A | 9/1990 | Janchipraponvej et al. |
| 5,019,376 A | 5/1991 | Uick |
| 5,328,685 A | 7/1994 | Janchitraponvej et al. |
| 5,358,667 A | 10/1994 | Bergmann |
| 5,447,654 A * | 9/1995 | Millequant et al. ...... 252/186.25 |
| 5,456,863 A | 10/1995 | Bergmann |
| 5,587,155 A * | 12/1996 | Ochiai et al. ............... 424/70.28 |
| 5,693,255 A | 12/1997 | Okamoto et al. |
| 5,776,443 A | 7/1998 | Vinski et al. |
| 5,876,705 A | 3/1999 | Uchiyama et al. |
| 5,888,488 A | 3/1999 | Fukuchi |
| 5,990,233 A | 11/1999 | Barron et al. |
| 6,090,885 A * | 7/2000 | Kuo et al. ...................... 524/838 |
| 6,231,843 B1 * | 5/2001 | Hoelzel et al. ............. 424/70.19 |
| 6,358,502 B1 | 3/2002 | Tanabe et al. |

FOREIGN PATENT DOCUMENTS

| | | |
|---|---|---|
| EP | 0 384 415 | 8/1990 |
| EP | 1 023 888 | 8/2000 |
| JP | 56-129300 | 10/1981 |
| JP | 64-19013 | 1/1989 |
| JP | 1-197423 | 8/1989 |
| JP | 3-128309 | 5/1991 |
| JP | 4-279512 | 10/1992 |
| JP | 5-229919 | 9/1993 |
| JP | 5-271035 | 10/1993 |
| JP | 5-271036 | 10/1993 |
| JP | 6-80539 | 3/1994 |
| JP | 6-122614 | 5/1994 |
| JP | 7-2629 | 1/1995 |
| JP | 8-143429 | 6/1996 |
| JP | 8-157332 | 6/1996 |
| JP | 10-120526 | 5/1998 |
| JP | 2998027 | 11/1999 |
| JP | 2000-212045 | 1/2000 |
| JP | 2000-501430 | 2/2000 |
| JP | 2000-72628 | 3/2000 |
| JP | 2000-86454 | 3/2000 |
| JP | 2000-109411 | 4/2000 |
| JP | 2000-143459 | 5/2000 |
| JP | 2000-507976 | 6/2000 |
| WO | WO 94/02111 | 2/1994 |
| WO | WO 01/08654 | 2/2001 |

* cited by examiner

*Primary Examiner* — Gina C Yu

(74) *Attorney, Agent, or Firm* — Oblon, Spivak, McClelland, Maier & Neustadt, L.L.P.

(57) ABSTRACT

Provided is a hair cosmetic composition which comprises the following components (A) to (D):
(A): an organic acid,
(B): an organic solvent selected from aromatic alcohols, polyols and carbonates,
(C): a cationic surfactant, and
(D): a higher alcohol, and
water and has a pH ranging from 2 to 6.
The hair cosmetic composition has excellent effects for repairing or preventing hair damage caused by coloring, permanent waving or blow drying and features good feeling upon use and luster improving effect.

11 Claims, No Drawings

HAIR COSMETIC COMPOSITION

TECHNICAL FIELD

The present invention relates to a hair cosmetic composition which has excellent effects for repairing or preventing hair damage caused by coloring or blow drying, has good feeling upon use and is effective for improving the luster and shine of the hair.

BACKGROUND ART

With recent popularization of hair coloring, damage after treatment with a coloring system (one-part type or two-part type) such as dryness or difficulty in styling of the hair has drawn attentions. The permanent waved hair also suffers such damage. The hair damage due to coloring or permanent waving treatment is said to occur because pores appear inside of the hair by chemical factors of the hair dye or permanent waving agent applied to the hair.

The hair loses its luster and moisture even by blow drying after shampooing. Such damage is found to occur because the inside of the hair becomes porous by the heat from a drier (Fragrance Journal, No. 6, 11(2000)).

For improving the touch feel of the shampooed hair, a hair cosmetic composition such as hair rinse, hair conditioner or hair treatment has been used. This hair cosmetic composition contains a cationic surfactant. Since single use of it is not sufficient for improving touch feel such as flexibility, a higher alcohol has been used in combination. This higher alcohol imparts the hair with flexibility and oily feel, thereby attaining an improvement in the touch feel. Owing to its high melting point, however, addition of it makes preparation of a hair cosmetic composition cumbersome and moreover, the hair cosmetic composition thus prepared involves a problem in stability (Japanese Patent Application Laid-Open (Kokai) No. 2000-72628, etc.).

Various hair cosmetic compositions having an organopolysiloxane oxyalkylene copolymer, acrylic resin or the like incorporated therein in order to improve optical properties of the hair such as luster have been proposed (for example, Japanese Patent Application Laid-Open (Kokai) No. Sho 56-129300). In these cosmetic compositions, improvement of optical properties is attained by the action of such a component on cuticles existing on the hair surface or in the vicinity thereof and its effect is only temporary and is not sufficient. In addition, a hair cosmetic composition for imparting the hair with luster by using a cationic surfactant in combination with a polyhydric alcohol, hydroxypropyl cellulose or the like is also proposed (Japanese Patent Publication No. 2998027), but it involves a problem in the touch feel upon application to the hair.

DISCLOSURE OF THE INVENTION

An object of the present invention is to provide a hair cosmetic composition which is capable of repairing pores formed inside of the colored, permanent waved or blow dried hair or preventing formation of them; is capable of imparting the hair with flexibility and oil feel, and in turn, smooth touch and improving optical properties of the hair such as luster, thus having excellent hair conditioning effects; is excellent in feeling upon use when applied to the hair; and has good stability.

The present inventors have found that a hair cosmetic composition capable of satisfying the above-described requirements is available by using an organic acid, a specific organic solvent, a cationic surfactant and a higher alcohol in combination and adjusting its pH within a specific range.

In one aspect of the present invention, there is thus provided a hair cosmetic composition which comprises the following components (A) to (D):

(A): an organic acid,
(B): an organic solvent selected from aromatic alcohols, polyols and carbonates,
(C): a cationic surfactant, and
(D): a higher alcohol, and
water and has a pH ranging from 2 to 6.

In another aspect of the present invention, there is also provided a method for repairing pores formed inside of the colored, permanent waved or blow dried hair; or a method for preventing formation of pores inside of the colored, permanent waved or blow dried hair, each method being characterized by the application of the above-mentioned hair cosmetic composition to hair.

BEST MODE FOR CARRYING OUT THE INVENTION

Examples of the organic acid to be used as the component (A) include alkylsulfuric acids, alkylphosphoric acids, monocarboxylic acids, dicarboxylic acids, hydroxycarboxylic acids and polycarboxylic acids. Of these, carboxylic acids are preferred, with dicarboxylic acids and hydroxycarboxylic acids being especially preferred.

Specific examples of the dicarboxylic acids include malonic acid, succinic acid, glutaric acid, adipic acid, maleic acid, fumaric acid and phthalic acid, with maleic acid being especially preferred, while those of the hydroxycarboxylic acids include glycolic acid, lactic acid, hydroxyacrylic acid, oxybutyric acid (particularly, α-oxybutyric acid), glyceric acid, malic acid, tartaric acid and citric acid. Of these, α-hydroxycarboxylic acids, especially, lactic acid and malic acid are preferred.

As the component (A), two or more of the above-exemplified ones may be used in combination. The content of the component (A) is preferably 0.1 to 20 wt. % (which will hereinafter be called "%", simply), more preferably 0.2 to 15%, especially 0.2 to 10%, each based on the whole composition.

Examples of the organic solvent serving as the component (B) include benzyl alcohol, benzyloxyethanol, propylene carbonate, and polypropylene glycol. As polypropylene glycol, preferred is that having an average molecular weight (as measured by GPC) of 200 to 700, especially 300 to 500.

The content of the component (B) is preferably 0.1 to 20%, more preferably 0.5 to 10%, especially 1 to 10% based on the whole composition.

As the cationic surfactant serving as the component (C), preferred is that represented by the following formula:

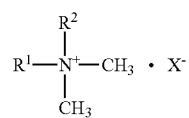

[wherein, $R^1$ and $R^2$ each independently represents a hydrogen atom, a $C_{1-28}$ alkyl group or a benzyl group, with the proviso that $R^1$ and $R^2$ do not represent a hydrogen atom or a benzyl group at the same time, and $X^-$ represents an anion]. It is preferred that one of $R^1$ and $R^2$ represents a $C_{16-24}$ alkyl group, especially a $C_{22}$ alkyl group, particularly linear alkyl group, while the other one represents a $C_{1-3}$ alkyl, particularly methyl group. Examples of the anion $X^-$ include halide ions such as chloride ions and bromide ions, and organic anions such as ethyl sulfate ions and methyl carbonate ions. Among them, halide ions, particularly, chloride ions are preferred.

As the component (C), mono(long-chain alkyl) quaternary ammonium salts are preferred. Specific examples include cetyltrimethylammonium chloride, stearyltrimethylammonium chloride, arachyltrimethylammonium chloride and behenyltrimethylammonium chloride, with behenyltrimethylammonium chloride being especially preferred. These mono (long-chain alkyl) quaternary ammonium salts usually have a distribution in the number of the carbon atoms of their long-chain alkyl group. The narrower distribution is preferred. More specifically, the content of the compound contained most in the component (C) is preferably 70 to 100%, especially 80 to 100%.

As the component (C), two or more of the above-described ones may be used in combination. Its content is preferably 0.5 to 10%, more preferably 1 to 10%, especially 2 to 10% based on the whole composition.

As the component (D), higher alcohols having a $C_{12-28}$ alkyl group, more preferably, a $C_{16-24}$ alkyl group, especially a $C_{22}$ alkyl group are preferred. As this alkyl group, a linear one is preferred.

Specific examples of the component (D) include cetyl alcohol, stearyl alcohol, arachyl alcohol and benehyl alcohol, with behenyl alcohol being especially preferred. These higher alcohols usually have a distribution in the number of carbon atoms of their long-chain alkyl group. The narrower distribution is preferred. More specifically, the content of the compound contained most in the component (D) is preferably 70 to 100%, especially 80 to 100%.

As the component (D), two or more of the above-described higher alcohols may be used. The content of it is preferably 1 to 20%, more preferably 1 to 10%, especially 2 to 10% based on the whole composition.

It is preferred from the viewpoint of the smoothness upon rinsing that the compounds contained most in the components (C) and (D), that is, compounds which occupy 70 to 100%, especially 80 to 100% of the components (C) and (D), respectively, have the same long-chain alkyl group, especially, a behenyl group.

The hair cosmetic composition of the present invention preferably contains a silicone as the component (E). Examples of the silicone include dimethyl polysiloxane, alkyl-modified polysiloxane, fluorine-modified polysiloxane, polyoxyalkylene-modified polysiloxane, carboxylic-acid-modified polysiloxane, alcohol-modified polysiloxane, epoxy-modified polysiloxane and cyclic dimethyl polysiloxane. Of these, dimethyl polysiloxane is preferred.

The hair cosmetic composition of the present invention preferably has a pH (25° C.) of 2.0 to 6.0, especially 2.5 to 4.5 for imparting the hair with luster. Its pH can be adjusted by an acidic substance, for example, an organic acid exemplified as the component (A) such as citric acid or lactic acid, or an inorganic acid, or a basic substance such as sodium hydroxide.

The hair cosmetic composition of the present invention can be prepared in any one of the forms of an aqueous solution, ethanol solution, emulsion, suspension, gel composition, liquid crystal composition, solid and aerosol. The hair cosmetic composition of the present invention can be used as a hair rinse, hair conditioner, hair treatment, hair pack, hair cream, conditioning mousse, hair mousse, hair spray, shampoo or leave-on treatment. Especially, it is suited for use as a washing-off type such as hair rinse, hair conditioner or hair treatment.

EXAMPLES

Example 1

The hair conditioners shown in Table 1 were prepared. The disappearance ratio of pores inside of the hair was measured; and smoothness of the hair upon rinsing, and smoothness of the hair, improvement in luster, dryness and styling ease of the hair after drying were evaluated. The results are shown in Table 1.

(i) Disappearance Ratio of Pores Inside of the Hair

A hair bundle (0.5 g) damaged by coloring was washed with 1 g of a plain shampoo (prepared using sodium polyoxyethylene (2.5) laurylether sulfate and diethanolamide). After water was drained off roughly, 1 g of a hair conditioner was applied to the hair bundle. The resulting hair bundle was allowed to stand for 1 minute, followed by further application of 4 g of the hair conditioner. It was then allowed to stand at 35 C for 15 minutes. The hair bundle was rinsed with running water for 15 seconds, towel dried and hot-air dried by a drier for 1 minute (this hair treatment corresponds to successive use of the hair conditioner for 1 week). After this hair treatment was repeated 4 times in total, the disappearance ratio of pores inside of the hair was determined.

Measurement of Pores

The hair was exposed to a light irradiated obliquely (angle: 15 to 60 degrees between the hair axis and light irradiation axis from a light source) from the hair root direction and observed from a direction on the same plane with the hair axis and light irradiation axis and at the same time, vertical to the hair axis by using a simple measuring microscope ("WIDE STAND MICRO", product of PEAK, ×10). This method makes it possible to remove a specular reflection light on the surface of the hair, which otherwise disturbs observation, thereby permitting observation of only the porous structure at the medulla as white streaks at the center portion of the hair when the hair has pores formed therein ("Fragrance Journal, No. 6, 11(2000)"). Before treatment, the whole length of the porous portion observed at the medulla as white streaks was measured. The hair after treatment was subjected to similar measurement. From the ratio of pores before treatment to those after treatment, the disappearance ratio or formation ratio of pores was determined.

(ii) Evaluation Methods of Smoothness, Improvement of Luster, Dryness and Styling Ease of the Hair A hair bundle (20 g) was washed sufficiently with 1 g of a plain shampoo (prepared using sodium polyoxyethylene (2.5) laurylether sulfate and diethanolamide). After water was drained off roughly, 2 g of a hair conditioner was applied to the hair bundle. The hair bundle was rinsed for 30 seconds with water of 40° C. running at 6 liter/min, towel dried and dried sufficiently by a hot wind of a drier for 2 to 3 minutes.

Organoleptic evaluation was conducted by a panel of 20 experts in accordance with the below-described standards and ranking was made based on the average of their scores.

Smoothness (Upon Rinsing and After Drying)
- 4: The hair is markedly smooth.
- 3: The hair is very smooth.
- 2: The hair is smooth.
- 1: The hair is slightly smooth.
- 0: The hair is not smooth.

Improvement of Luster (After Drying)
- 4: Marked improvement in luster is observed.
- 3: Improvement in luster is observed.
- 2: Slight improvement in luster is observed.
- 1: No improvement in luster is observed.
- 0: Luster is lost.

Dryness (After Drying)
- 4: Dryness is not observed at all.
- 3: Dryness is not observed.
- 2: Slight dryness is observed.
- 1: Dryness is observed.
- 0: Much dryness is observed.

Styling Ease (After Drying)
- 4: The hair can be styled at excellent ease.
- 3: The hair can be styled at ease.
- 2: The hair can be styled.
- 1: The hair cannot be styled at ease.
- 0: The hair cannot be styled.

[Rank]
- A: 3.50 to 4.00 on average
- B: 3.00 to 3.45 on average
- C: 2.00 to 2.95 on average
- D: 1.00 to 1.95 on average
- E: 0.00 to 0.95 on average

TABLE 1

|  | Invention Product | | Comparative Product | (%) |
|---|---|---|---|---|
|  | 1 | 2 | 1 | 2 |
| Behenyltrimethylammonium chloride | 1.7 | | 1.7 | |
| Stearyltrimethylammonium chloride | | 1.2 | | 1.2 |
| Cetanol | | 3.5 | | 3.5 |
| Behenyl alcohol | 5.1 | | 5.1 | |
| Benzyl oxyethanol | 0.3 | 0.5 | 0.3 | |
| PPG400 (molecular weight: 400) | 1 | | 1 | |
| Malic acid | 1 | | | |
| Lactic acid | | 4 | | 4 |
| Hydroxyethyl cellulose | 0.2 | 0.2 | 0.2 | 0.2 |
| 48% NaOH | 0.2 | 0.2 | | 1.5 |
| Purified water | Balance | Balance | Balance | Balance |
| pH (25° C.) | 3.3 | 3.2 | 4.0 | 7.0 |
| Disappearance ratio of pores inside of the hair (%) | 72 | 70 | 8 | 11 |
| Smoothness of the hair upon rinsing | A | B | A | B |
| Smoothness of the hair after drying | A | B | A | B |
| Hair luster improving effect | A | A | D | C |
| Dryness of the hair after drying | A | A | D | D |
| Styling ease of the hair after drying | A | A | D | D |

From the hair treated with the hair conditioners of the present invention, marked disappearance of pores was recognized. According to the organoleptic evaluation, the hair treated with them had excellent smoothness, improved luster, and good styling ease without dryness.

Example 2

In a similar manner to (i) of Example 1, treatment was performed four times (hot-air drying time by a drier was increased to 5 minutes) by using 0.5 g of a hair bundle free from pores inside of the hair and hair conditioners of the invention product and comparative product. The formation ratio of pores after treatment was measured in a similar manner and results are shown in Table 2.

TABLE 2

|  | | Formation ratio of pores (%) |
|---|---|---|
| Invention products | 1 | 0 |
|  | 2 | 0 |
| Comparative products | 1 | 35 |
|  | 2 | 35 |

From the hair treated with the conditioner according to the present invention, formation of pores was not recognized, indicating that they have marked effects for preventing formation of pores.

According to the organoleptic evaluation, use of the hair conditioner according to the present invention prevented dryness of the hair, thereby bringing about good styling ease even after drier treatment for 5 to 10 minutes.

Examples 3

Hair conditioners shown in Table 3 were prepared. As in Example 1, a disappearance ratio of pores inside of the hair was measured and smoothness of the hair upon rinsing, and smoothness of the hair, improvement of luster, dryness and styling ease after drying were evaluated. The results are shown in Table 3.

TABLE 3

|  | Invention products | | | | Comparative products (%) | |
| --- | --- | --- | --- | --- | --- | --- |
|  | 3 | 4 | 5 | 6 | 3 | 4 |
| Malic acid |  | 2 | 2 | 0.5 |  | 2 |
| Lactic acid | 4 |  | 1 |  |  | 1 |
| Polypropylene glycol (molecular weight: 400) | 1 | 2 | 0.5 | 2 |  |  |
| Behenyltrimethylammonium chloride | 1.7 |  | 2.25 | 1.7 | 1.7 | 2.25 |
| Stearyltrimethylammonium chloride |  | 1.2 |  |  |  |  |
| Cetanol |  | 3.5 | 0.3 |  |  | 0.3 |
| Behenyl alcohol | 5.1 |  | 7.2 | 5 | 5.1 | 7.2 |
| Methyl polysiloxane (SH500-5000CS) | 3 | 2 | 2 | 2.5 | 3 |  |
| Isopropyl palmitate | 1 | 1.5 | 1 | 0.5 | 1 |  |
| Dipentaerythritol fatty acid ester | 0.1 | 0.2 | 0.3 | 0.2 | 0.1 |  |
| BenzyloxyethanOl | 0.3 |  | 0.5 | 0.3 | 0.3 | 0.5 |
| Hydroxyethyl cellulose | 0.2 |  | 0.2 |  | 0.2 | 0.2 |
| Polyethylene glycol (molecular weight: 100000) |  | 0.1 |  | 0.05 |  |  |
| 48% NaOH | 0.2 | 0.2 | 0.25 |  | 0.2 | 0.25 |
| Purified water | Balance | Balance | Balance | Balance | Balance | Balance |
| pH (25° C.) | 3.3 | 3.2 | 3.3 | 3.0 | 3.3 | 3.3 |
| Disappearance ratio of pores inside of the hair (%) | 70 | 75 | 80 | 70 | 0 | 10 |
| Smoothness upon rinsing | A | B | A | A | C | C |
| Smoothness after drying | A | B | A | A | C | D |
| Hair luster improving effect | A | A | A | B | E | C |
| Dryness of the hair after drying | A | A | A | A | B | C |
| Styling ease of the hair after drying | A | A | A | A | B | C |

From the hair treated with any one of the hair conditioners according to the present invention, marked disappearance of pores was recognized. According to the organoleptic evaluation, the hair treated by them had excellent smoothness, improved luster, and good styling ease without dryness. In addition, they were stable for a long period of time.

Example 4

A hair conditioner (pH 3.0) having the below-described composition was prepared.

|  | (%) |
| --- | --- |
| Behenyltrimethylammonium chloride (behenyl content: 85%) | 1.7 |
| Behenyl alcohol (behenyl content: 85%) | 5.0 |
| Isopropyl palmitate | 0.5 |
| Dipentaerythritol fatty acid ester | 0.2 |
| Methyl polysiloxane ("Silicone KHS-3", trade name; product of Shin-etsu Chemical) | 2.5 |
| Benzyl oxyethanol | 0.3 |
| Polypropylene glycol 400 (PPG400) | 2.0 |
| Malic acid | 0.5 |
| Hydroxyethyl cellulose | 0.2 |
| Purified water | Balance |

It has been found that this hair conditioner had good touch feeling during the period from application to rinsing, and even after drying, had good styling ease without dryness. The pore disappearance ratio as measured in a similar manner to Example 1 was 78%, indicating a marked pore repairing effect.

The pore disappearance ratio of a composition obtained by using the above-described components except benzyl oxyethanol, PPG400 and malic acid, balancing the mixture with purified water, and adjusting its pH to 5.0 was measured, which resulted in 0%, indicating no pore repairing effect.

Example 5

A hair treatment (pH 3.3) having the below-described composition was prepared.

|  | (%) |
| --- | --- |
| Stearylamidopropyldimethylamine•lactate | 2.4 |
| Cetanol | 7.0 |
| Isopropyl palmitate | 1.0 |
| Dipentaerythritol fatty acid ester | 0.3 |
| Methyl polysiloxane ("Silicone KHS-3", trade name; product of Shin-etsu Chemical) | 2.5 |
| Benzyloxyethanol | 0.5 |
| Malic acid | 1.0 |
| Hydroxyethyl cellulose | 0.2 |
| 48% Aqueous solution of sodium hydroxide | 0.15 |
| Purified water | Balance |

It has been found that this hair treatment had good touch feeling during the period from application to rinsing, and had good styling ease without dryness after drying. The pore formation ratio as measured in a similar manner to Example 2 was 0% after 4-week use, indicating a marked pore preventing effect.

The pore formation ratio of a composition prepared by using the above-described components except benzyloxyethanol and malic acid, balancing the mixture with purified water, and adjusting its pH to 4.5 was measured, which resulted in 40%, indicating no pore preventing effect.

The invention claimed is:

1. A hair cosmetic composition which comprises the following components (A) to (E):
   (A): 0.2-4.0 wt. % of at least one of lactic and malic acid,
   (B): 0.1-10 wt. % of polypropylene glycol having an average molecular weight, as measured by GPC, of 200-700,
   (C): 0.5-10 wt. % of at least one cationic surfactant,
   (D): 1-10 wt. % of at least one $C_{12}$-$C_{28}$ alcohol, and water, and which composition has a pH ranging from 2.5 to 4.5, and
   (E): a silicone.

2. The hair cosmetic composition of claim 1, wherein the alcohol contained most in component (D) makes up 70 to 100 wt. % of component (D), and the cationic surfactant contained most in component (C) makes up 70 to 100 wt. % of component (C), wherein the alkyl group in said alcohol contained most in component (D) has the same number of carbons as an alkyl group in said cationic surfactant contained most in component (C).

3. A hair cosmetic composition which comprises the following components (A) to (D):
   (A): 0.2-4.0 wt. % of at least one of lactic and malic acid,
   (B): 0.1-10 wt. % of polypropylene glycol having an average molecular weight, as measured by GPC, of 200-700,
   (C): at least one cationic surfactant, and
   (D): at least one $C_{12}$-$C_{28}$ alcohol, and water, and which composition has a pH ranging from 2.5 to 4.5, wherein said hair cosmetic composition has the capability of repairing pores formed, or preventing formation of pores, inside of colored, permanent waved or blow dried hair, when applied to such hair.

4. The hair cosmetic composition of claim 1, wherein component (A) comprises malic acid.

5. The hair cosmetic composition of claim 1, wherein components (A) and (B) are present in a weight ratio (A)/(B) of 1/4 to 6/1.

6. The hair cosmetic composition of claim 1, wherein component (C) is a long chain mono quaternary ammonium salt containing a C16-C24 straight chain alkyl group and present in an amount of 2-10 wt. %.

7. The hair cosmetic composition of claim 1, wherein component (D) is a C12-C24 alcohol and present in an amount of 2-10 wt. %.

8. A method comprising applying the hair cosmetic composition of claim 1 to colored, permanent waved or blow dried hair in need of repairing pores formed, or preventing formation of pores, inside of said hair.

9. A method comprising applying the hair cosmetic composition of claim 3 to colored, permanent waved or blow dried hair in need of repairing pores formed, or preventing formation of pores, inside of said hair.

10. The hair cosmetic composition of claim 1, wherein the polypropylene glycol has an average molecular weight, as measured by GPC, of 300-500.

11. The hair cosmetic composition of claim 3, wherein the polypropylene glycol has an average molecular weight, as measured by GPC, of 300-500.

* * * * *